US010961203B2

(12) United States Patent
Liu et al.

(10) Patent No.: US 10,961,203 B2
(45) Date of Patent: Mar. 30, 2021

(54) CRYSTALLINE FORMS OF 3-Z-[1-(4-(N-((4-METHYL-PIPERAZIN-1-YL)-METHYLCARBONYL)-N-METHYL-AMINO)-PHENYLAMINO)-1-PHENYL-METHYLENE]-6-METHOXYCARBONYL-2-INDOLINONE

(71) Applicant: Allgenesis Biotherapeutics Inc., Taipei (CN)

(72) Inventors: Fei Liu, Nanjing (CN); Cuixia Zhang, Nanjing (CN); Weiming Jiang, Nanjing (CN); Chin-Yu Lai, Taipei (TW); Tan Nguyen, Taipei (TW); Haolong Zhang, Nanjing (CN)

(73) Assignee: Allgenesis Biotherapeutics Inc., Taipei (TW)

( * ) Notice: Subject to any disclaimer, the term of this patent is extended or adjusted under 35 U.S.C. 154(b) by 0 days.

(21) Appl. No.: 16/570,710

(22) Filed: Sep. 13, 2019

(65) Prior Publication Data

US 2020/0002294 A1 Jan. 2, 2020

Related U.S. Application Data

(63) Continuation of application No. PCT/CN2017/076648, filed on Mar. 14, 2017.

(51) Int. Cl.
*C07D 241/04* (2006.01)
*A61K 9/00* (2006.01)

(52) U.S. Cl.
CPC .......... *C07D 241/04* (2013.01); *A61K 9/0048* (2013.01); *C07B 2200/13* (2013.01)

(58) Field of Classification Search
CPC .................................................. C07D 241/04
See application file for complete search history.

(56) References Cited

U.S. PATENT DOCUMENTS

| 7,119,093 B2 * | 10/2006 | Roth ...................... A61P 43/00 514/254.09 |
| 8,304,541 B2 * | 11/2012 | Merten ................ C07D 209/34 544/373 |
| 9,920,033 B2 * | 3/2018 | Xi .......................... C07C 309/30 |
| 10,292,965 B2 * | 5/2019 | Wang ..................... A61P 11/00 |
| 2017/0174625 A1 | 6/2017 | Xu |

FOREIGN PATENT DOCUMENTS

| CN | 104844499 A | 8/2015 |
| CN | 105461609 A | 4/2016 |
| CN | 105837493 A | 8/2016 |
| CN | 106748960 A | 5/2017 |
| CN | 106748961 A | 5/2017 |
| WO | 2009071523 A1 | 6/2009 |
| WO | 2016178064 A1 | 11/2016 |
| WO | 2016209555 A1 | 12/2016 |
| WO | 2017016530 A1 | 2/2017 |
| WO | 2017077551 A2 | 5/2017 |

OTHER PUBLICATIONS

International Search Report issued for PCT/CN2017/076648, dated Dec. 13, 2017, 3 pages.

* cited by examiner

*Primary Examiner* — Kamal A Saeed
(74) *Attorney, Agent, or Firm* — OPES IP Consulting Co., Ltd.

(57) ABSTRACT

Crystalline forms of free base 3-Z-[1-(4-(N-((4-methyl-piperazin-1-yl)-methylcarbonyl)-N-methyl-amino)-phenylamino)-1-phenyl-methylene]-6-methoxycarbonyl-2-indolinone and preparation methods thereof are provided; the pharmaceutical formulations containing the crystalline forms and their use in the treatment of diseases, particularly angiogenic eye diseases are also provided.

20 Claims, 12 Drawing Sheets

CRYSTALLINE FORMS OF 3-Z-[1-(4-(N-((4-METHYL-PIPERAZIN-1-YL)-METHYLCARBONYL)-N-METHYL-AMINO)-PHENYLAMINO)-1-PHENYL-METHYLENE]-6-METHOXYCARBONYL-2-INDOLINONE

CROSS-REFERENCE TO RELATED APPLICATIONS

This application is a continuation of International Application No. PCT/CN2017/076648, filed on Mar. 14, 2017, which is hereby incorporated by reference in its entirety.

TECHNICAL FIELD

The invention relates to a novel crystalline form of free base 3-Z-[1-(4-(N-((4-methyl-piperazin-1-yl)-methylcarbonyl)-N-methyl-amino)-phenylamino)-1-phenyl-methylene]-6-methoxycarbonyl-2-indolinone and its preparation method, pharmaceutical formulations containing the crystalline form and their use as medicament.

BACKGROUND

3-Z-[1-(4-(N-((4-methyl-piperazin-1-yl)-methylcarbonyl)-N-methyl-amino)-phenylamino)-1-phenyl-methylene]-6-methoxycarbonyl-2-indolinone, known by its drug name Nintedanib, is an effective inhibitor of the receptor tyrosine kinase family (RTK). Nintedanib can inhibit platelet-derived growth factor receptors (PDGFR), fibroblast growth factor receptors (FGFR), vascular endothelial growth factor receptors (VEGFR), and Fms-like tyrosine kinase-3 (FLT3). FGFR, PDGFR, and VEGFR are involved in Idiopathic Pulmonary Fibrosis (IPF) pathogenesis, and by blocking these signal transduction pathways involved in fibrosis progression, Nintedanib can slow down the progression of IPF diseases by reducing the rate of lung function deterioration. WO 2016/209555 discloses an ophthalmic formulation containing Nintedanib for the treatment of ocular surface disorders.

SUMMARY OF THE INVENTION

An objective of the present invention is to provide a novel crystalline form of Nintedanib (chemical name: 3-Z-[1-(4-(N-((4-methyl-piperazin-1-yl)-methylcarbonyl)-N-methyl-amino)-phenylamino)-1-phenyl-methylene]-6-methoxycarbonyl-2-indolinone).

Another objective of the present invention is to provide a method for preparing the crystalline form of Nintedanib.

Another objective of the present invention is to provide a pharmaceutical formulation containing the crystalline form of Nintedanib.

Another objective of the present invention is to provide the use of the crystalline form of Nintedanib and the formulation thereof.

In one aspect, the present invention provides a crystalline form of free base 3-Z-[1-(4-(N-((4-methyl-piperazin-1-yl)-methylcarbonyl)-N-methyl-amino)-phenylamino)-1-phenyl-methylene]-6-methoxycarbonyl-2-indolinone, that is, a crystalline form of Nintedanib. The crystalline form of Nintedanib provided by the present invention includes Form B, Form C, Form D, Form E, and Form F.

In some specific embodiments of the present invention, the crystalline form of Nintedanib according to the invention is characterized by having an X-ray powder diffraction (XRPD) pattern having a peak at 2θ value of 6.4±0.2, and has at least one peak at 2θ value selected from 16.6±0.2, 17.4±0.2, 17.8±0.2, and 19.9±0.2. Such crystalline form includes Form C, Form D, Form E, and Form F.

In some specific embodiments of the present invention, the crystalline form of Nintedanib according to the invention is characterized by having an XRPD pattern with peaks at 2θ values of 6.4±0.2, 16.6±0.2, 17.4±0.2, 17.8±0.2, and 19.9±0.2 in the XRPD spectrum. Such crystalline form includes Form C, Form E, and Form F.

In some specific embodiments of the present invention, the crystalline form of Nintedanib according to the invention is characterized by having an XRPD pattern with peaks at 2θ values of 6.4±0.2, 12.0±0.2, 16.6±0.2, 17.4±0.2, 17.8±0.2, and 19.9±0.2. Such crystalline form includes Form E and Form F.

In some specific embodiments of the present invention, the crystalline form of Nintedanib according to the invention is characterized by having an XRPD pattern with peaks at 2θ values of 6.4±0.2, 12.0±0.2, 16.6±0.2, 17.4±0.2, 17.8±0.2, and 19.9±0.2; furthermore, this crystalline form has a melting temperature of 245° C.±5° C. In the present invention, this crystalline form is designated as Form E.

In some specific embodiments of the present invention, the crystalline form of Nintedanib according to the invention is characterized by having an XRPD pattern with peaks at 2θ values of 6.4±0.2, 12.0±0.2, 16.6±0.2, 17.4±0.2, 17.8±0.2, and 19.9±0.2; furthermore, this crystalline form has a melting temperature of 255° C.±5° C. In the present invention, this crystalline form is designated as Form F.

In some specific embodiments of the present invention, the crystalline form of Nintedanib according to the invention is characterized by having an XRPD pattern with peaks at 2θ values of 6.4±0.2, 16.6±0.2, 17.4±0.2, 17.8±0.2, 19.9±0.2, and 23.3±0.2. In the present invention, the crystalline form having these peaks is designated as Form C.

In some specific embodiments of the present invention, the crystalline form of Nintedanib according to the invention is characterized by having an XRPD pattern with peaks at 2θ values of 4.8±0.2, 5.6±0.2, 6.4±0.2, 17.4±0.2, and 19.9±0.2. In the present invention, the crystalline form having these peaks in the XRPD spectrum is designated as Form D.

The present invention also provides another crystalline form of Nintedanib characterized by having an XRPD pattern with peaks at 2θ values of 11.2±0.2, 14.8±0.2, 16.4±0.2, 17.0±0.2, and 21.0±0.2. In the present invention, the crystalline form having these peaks in the XRPD spectrum is designated as Form B.

In some specific embodiments of the present invention, the crystalline form of Nintedanib according to the invention is Crystalline Form E, with an XRPD spectrum as shown in FIG. 12, FIG. 14, FIG. 19, FIG. 20, FIG. 21, or FIG. 22. In the present invention, "as shown in Figure n" means that the XRPD spectrum has peaks as indicated at the specific 2θ values±0.2 in Figure n.

Figure 13:
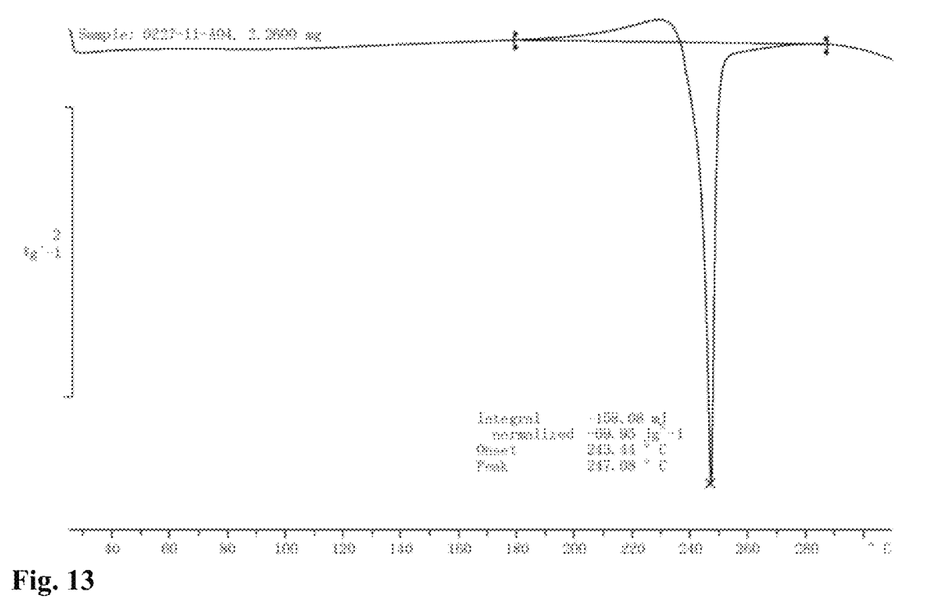
FIG. 13 is the DSC profile of Crystalline Form E of Nintedanib according to the invention (experimental No. 0227-11-A04).

In some specific embodiments of the present invention, the crystalline form of Nintedanib according to the invention is Crystalline Form E, and this crystalline form has a differential scanning calorimetry (DSC) profile as shown in FIG. 13.

Figure 15:
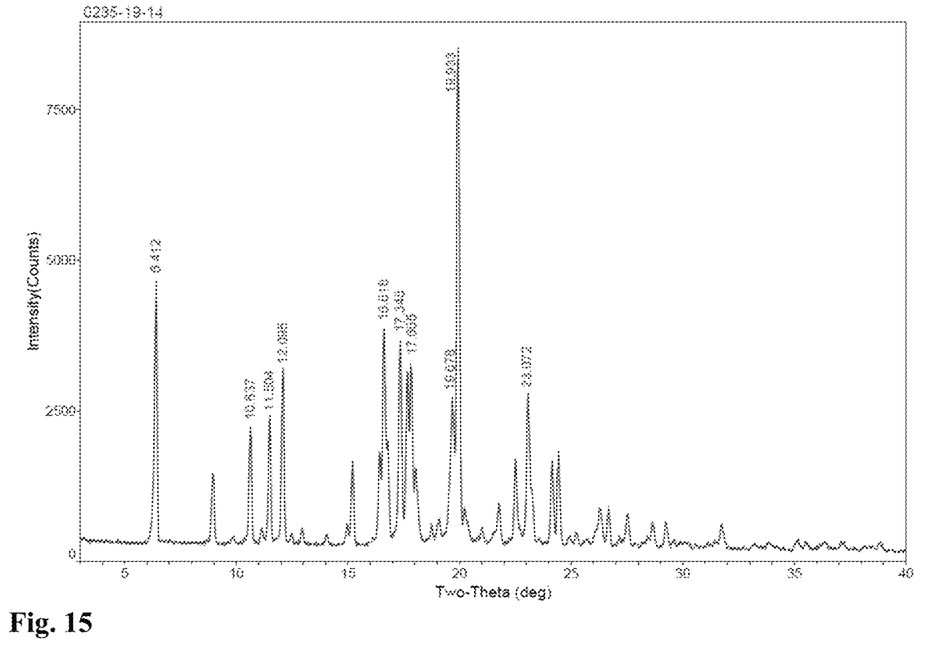
FIG. 15 is the XRPD spectrum of Crystalline Form F of Nintedanib according to the invention.
Figure 23:
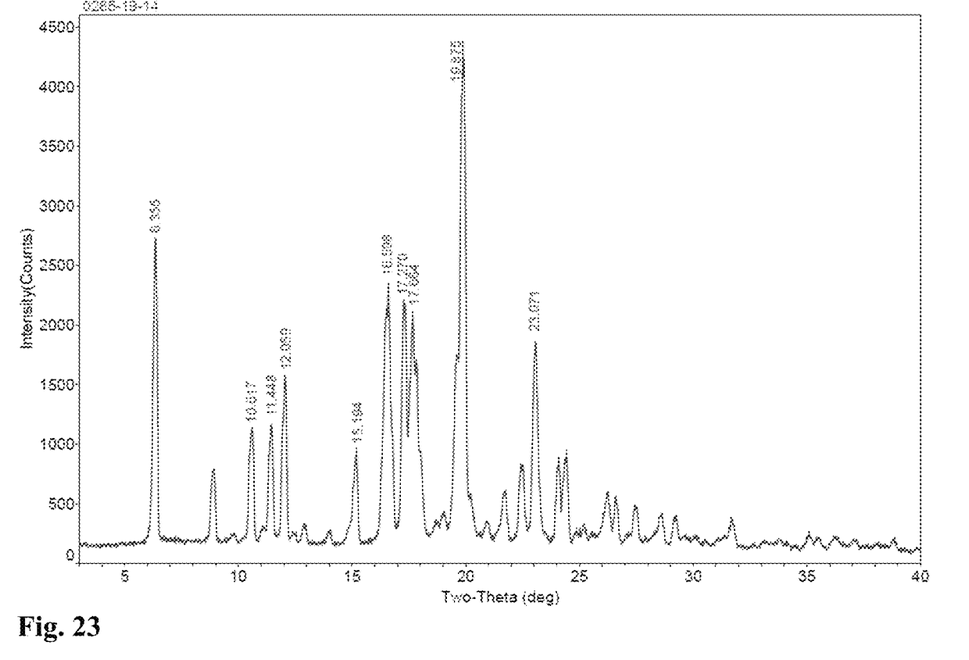
FIG. 23 is the XRPD spectrum of Crystalline Form F of Nintedanib after being kept at room temperature for 3 months in accordance with another Example of the present invention.

In some specific embodiments of the present invention, the crystalline form of Nintedanib according to the invention is Crystalline Form F, and the XRPD spectrum of this crystalline form is shown in FIG. 15 or FIG. 23.

Figure 16:
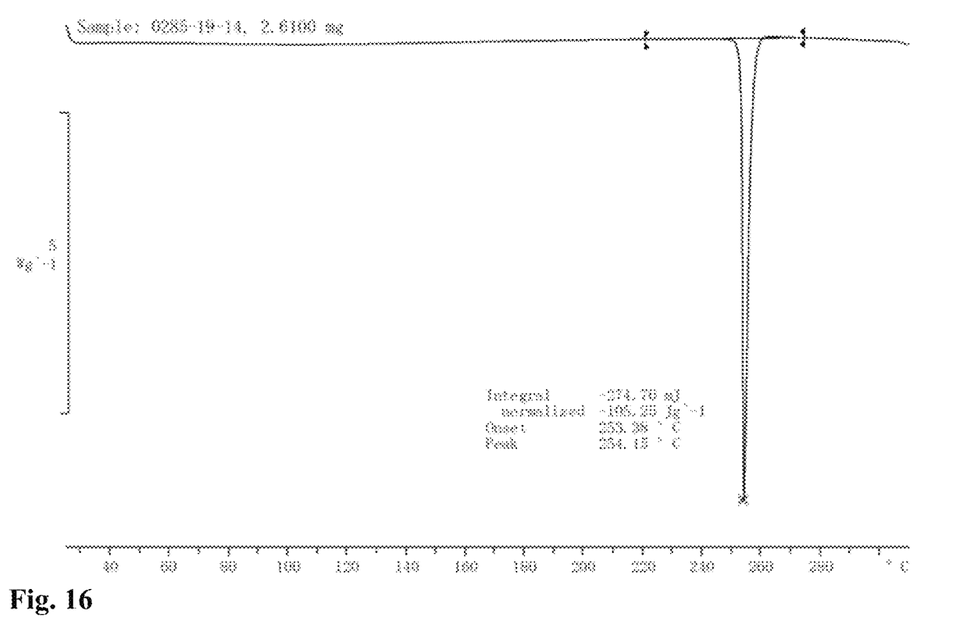
FIG. 16 is the DSC profile of Crystalline Form F of Nintedanib according to the invention.

In some specific embodiments of the present invention, the crystalline form of Nintedanib according to the invention is Crystalline Form F, and the DSC profile of this crystalline form is shown in FIG. 16.

In some specific embodiments of the present invention, the crystalline form of Nintedanib according to the invention is Crystalline Form C, and the XRPD spectrum of this crystalline form is shown in FIG. 3, FIG. 4, FIG. 5, FIG. 6, FIG. 7, FIG. 8, FIG. 9, FIG. 10, FIG. 17, or FIG. 18.

Figure 11:
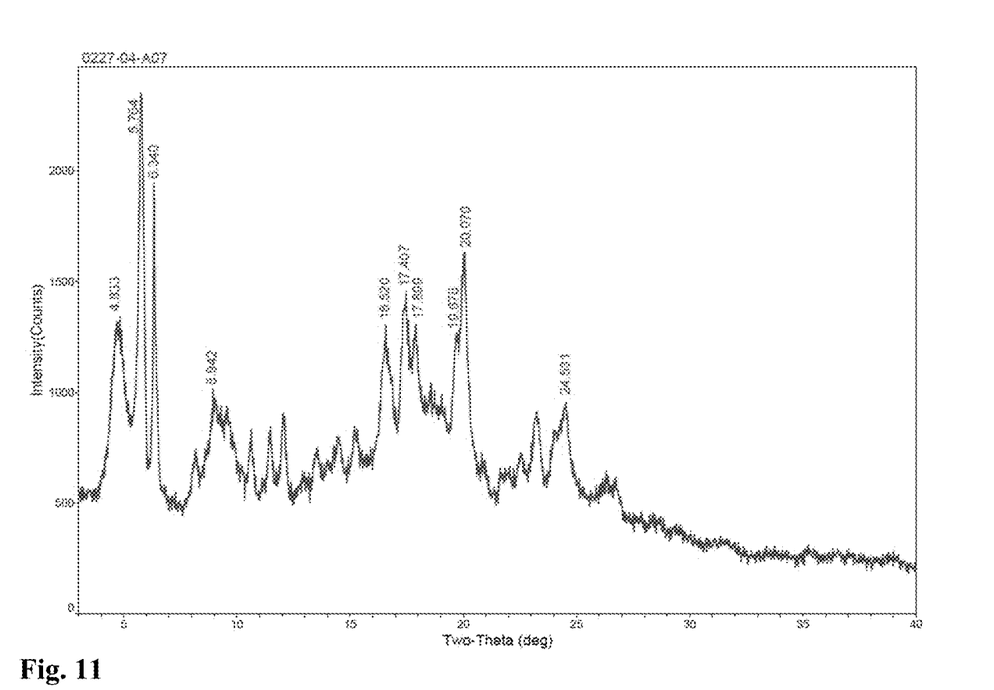
FIG. 11 is the XRPD spectrum of Crystalline Form D of Nintedanib according to the invention.

In some specific embodiments of the present invention, the crystalline form of Nintedanib according to the invention is Crystalline Form D, and the XRPD spectrum of this crystalline form is shown in FIG. 11.

Figure 1:
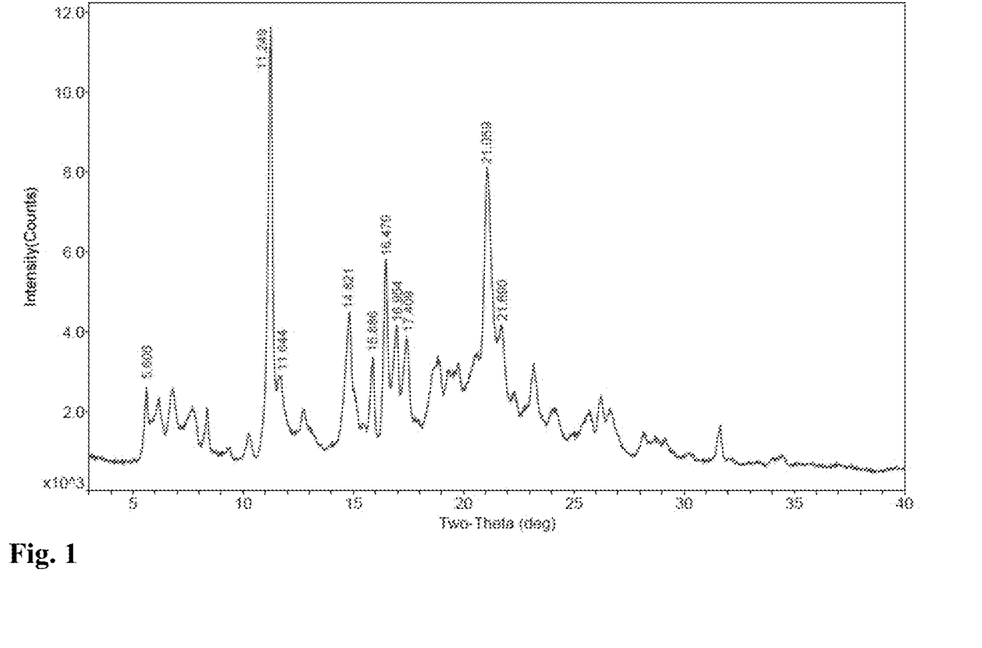
FIG. 1 is the XRPD spectrum of Crystalline Form B of Nintedanib according to the invention.

In some specific embodiments of the present invention, the crystalline form of Nintedanib according to the invention is Crystalline Form B, and the XRPD spectrum of this crystalline form is shown in FIG. 1.

In another aspect, the present invention also provides a method for preparing the crystalline form of Nintedanib according to the invention, wherein the crystalline forms of Nintedanib free base or particular salts that are commercially available as starting material are suspended in different solvent systems under stirring, followed by slow volatilization, so as to obtain various crystalline forms of Nintedanib according to the invention. In some specific embodiments of the present invention, the method for preparing the crystalline form of Nintedanib includes: adding Nintedanib ethanesulfonate to a saturated sodium carbonate aqueous solution, extracting with dichloromethane, neutralizing with water, drying the organic layer with anhydrous sodium sulfate, and evaporating the solvent to obtain Crystalline Form B of Nintedanib.

In some specific embodiments of the present invention, the method for preparing the crystalline form of Nintedanib includes: adding Nintedanib to acetone, followed by vortexing for a few minutes before filtering through a 0.22 μm organic filter film to obtain a filtrate, and evaporating the solvent from the filtrate to obtain a solid as Crystalline Form C of Nintedanib.

In some specific embodiments of the present invention, the method for preparing the crystalline form of Nintedanib includes: adding Nintedanib to a solvent, suspending with magnetic stirring, removing the supernatant by centrifugation, and volatilizing to obtain a solid as Crystalline Form C of Nintedanib. Specifically, the solvent is at least one selected from a group consisting of acetonitrile, isopropanol, n-propanol, 2-butanone, 1,4-dioxane/water mixed solvent, heptane, methanol/water mixed solvent, and acetone/water mixed solvent.

In some specific embodiments of the present invention, the method for preparing the crystalline form of Nintedanib includes: adding Nintedanib to dichloromethane, vortexing for a few minutes before filtering through a 0.22 μm organic filter membrane to obtain a filtrate, and evaporating the solvent from the filtrate to obtain a solid as Crystalline Form D of Nintedanib.

In some specific embodiments of the present invention, the method for preparing the crystalline form of Nintedanib includes: adding Crystalline Form A of Nintedanib to water or acetone/water (9/1, v/v), vortexing for a few minutes before filtering through a 0.22 μm filter membrane; adding Crystalline Form B of Nintedanib to the filtrate, vortexing and filtering through a 0.22 μm filter membrane; adding Crystalline Form C of Nintedanib to the filtrate, vortexing and filtering through a 0.22 μm filter membrane; adding Crystalline Forms A, B, and C of Nintedanib to the filtrate, followed by magnetically stirring, removing the supernatant by centrifugation, and volatilizing to obtain a solid as Crystalline Form E of Nintedanib.

In some specific embodiments of the present invention, the method for preparing the crystalline form of Nintedanib includes: adding Nintedanib ethanesulfonate to water, adjusting pH of the solution to about 10 with saturated sodium carbonate solution, adding dichloromethane to the suspension solution, stirring, allowing to stand for liquid separation, extracting the water layer with dichloromethane, combining the organic phase, washing the organic phase with water, separating the liquid, drying with anhydrous sodium sulphate, removing the solvent by distillation under reduced pressure, and drying to obtain a Nintedanib free base. The Nintedanib free base is then added to ethanol, suspended by stirring, filtered, and dried to obtain Crystalline Form F.

In some specific embodiments of the present invention, the method for preparing the crystalline form of Nintedanib includes: adding Crystalline Form F of Nintedanib to water, stirring homogenously with a magnetic stir bar before adding a trace amount of Crystalline Form E as seeding crystal, stirring with a magnetic stir bar at room temperature, centrifuging to obtain a solid which is then dried to obtain Crystalline Form E of Nintedanib.

In some specific embodiments of the present invention, the method for preparing the crystalline form of Nintedanib includes: mixing and dispersing Crystalline Form F of the Nintedanib with 0.2% tyloxapol solution, grinding the mixture of Nintedanib and tyloxapol together with 200 micron zirconia grinding beads, followed by centrifuging and drying, so as to obtain a solid as Crystalline Form E of Nintedanib.

The crystalline forms of Nintedanib according to the invention exhibit valuable pharmacological properties and can be used in pharmaceutical industry for producing pharmaceutical compositions useful in human medicine.

In another aspect, the present invention also provides the use of the crystalline form of Nintedanib in the preparation of a medicament, in particular in the preparation of a medicament for the treatment and/or prevention of eye diseases.

In addition, the present invention further provides pharmaceutical compositions containing the crystalline form of Nintedanib according to the invention.

In some specific embodiments of the present invention, the invention provides an ophthalmic formulation comprising the crystalline form of Nintedanib according to the invention (including at least one form of Crystalline Forms B, C, D, E, and F) and at least one pharmaceutically acceptable carriers.

Furthermore, the present invention also provides the use of the ophthalmic formulation in the preparation of medicaments for the treatment of eye diseases selected from: age-related macular degeneration (AMD), angiogenesis in the anterior part of the eye such as corneal angiogenesis following e.g. keratitis, corneal transplantation or keratoplasty, atrophic changes of retinal pigment epithelium (RPE), choroidal neovascularization (CNV), choroidal retinal vein occlusion, conjunctival degeneration (pinguecula) with slow proliferation, conjunctival papilloma, corneal angiogenesis due to hypoxia retinal detachment, diabetic macular edema, diabetic retinopathy, hyperemia, hyperemia associated with pterygium, hyperthyroidism-induced hyperemia, hypertrophic changes of retinal pigment epithelium (RPE), immune or surgery related dry eyes, intraretinal edema, macular edema, macular edema due to retinal vein occlusion, neovascular glaucoma (NVG), ocular cancer, pterygium conjunctivae, pterygium recurrence, Steven Johnson syndrome, stye, and subretinal edema.

In some specific embodiments of the present invention, the ophthalmic formulation containing the crystalline form of Nintedanib is used for treating angiogenic eye diseases.

The desired pharmacological effect can be achieved by administering the crystalline form of Nintedanib to the individual in need. For the purpose of the invention, the individual is preferably a mammal or human being in need of the treatment of a particular disorder or disease.

The crystalline form of Nintedanib according to the invention has the following advantageous effect: the crystalline form of Nintedanib according to the invention has an enhanced thermodynamic stability.

DETAILED DESCRIPTION OF THE INVENTION

The present invention is further described in details hereinafter by specific examples, but the invention is not limited to the following examples.

In each example, XRPD experiment was conducted using a Bruker D8 advance diffractometer, with a Cu Ka (wavelength 1.54056 Å) filled tube (40 kV, 40 mA) as the X-ray source having a wide angle goniometer, a 0.6 mm divergent slit, a 2.5° primary Sola slit, a 2.5° secondary Sola slit, an 8 mm anti-scattering slit, a 0.1 mm detector slit, and Lynx Eye detector, at room temperature. In a 2θ continuous scanning mode, the data acquisition was completed with a scanning speed of 2.4°/min and a scanning step of 0.02° in the range of 3° to 40°.

DSC experiment was carried out using TA Q200, Mettler DSC 1+ and Mettler DSC 3+; and data acquisition was completed under the protection of $N_2$ at a flow rate of 50 mL/min, with a temperature rise from room temperature to the degradation temperature with a speed of 10° C./min.

Examples of Crystalline Forms of Nintedanib and the Preparation Method Thereof

Example 1: Crystalline Form B of Nintedanib and its Preparation Method 22 g of Nintedanib ethanesulfonate (Shanghai Baiteyin Pharmaceutical Technology Co., Ltd.) was added to a saturated sodium carbonate aqueous solution, pH was adjusted to 9, and 20 mL dichloromethane was added thereto for extraction for three times; the resultant was washed three times to neutral with 30 mL water, and the organic layer was dried with anhydrous sodium sulfate. After drying for 0.5 h, the solvent was removed by rotary distillation under reduced pressure to obtain 20 g of Crystalline Form B of Nintedanib.

The XRPD spectrum of Crystalline Form B of Nintedanib is shown in FIG. 1.

Example 2: Crystalline Form C of Nintedanib and its Preparation Method

Figure 2:
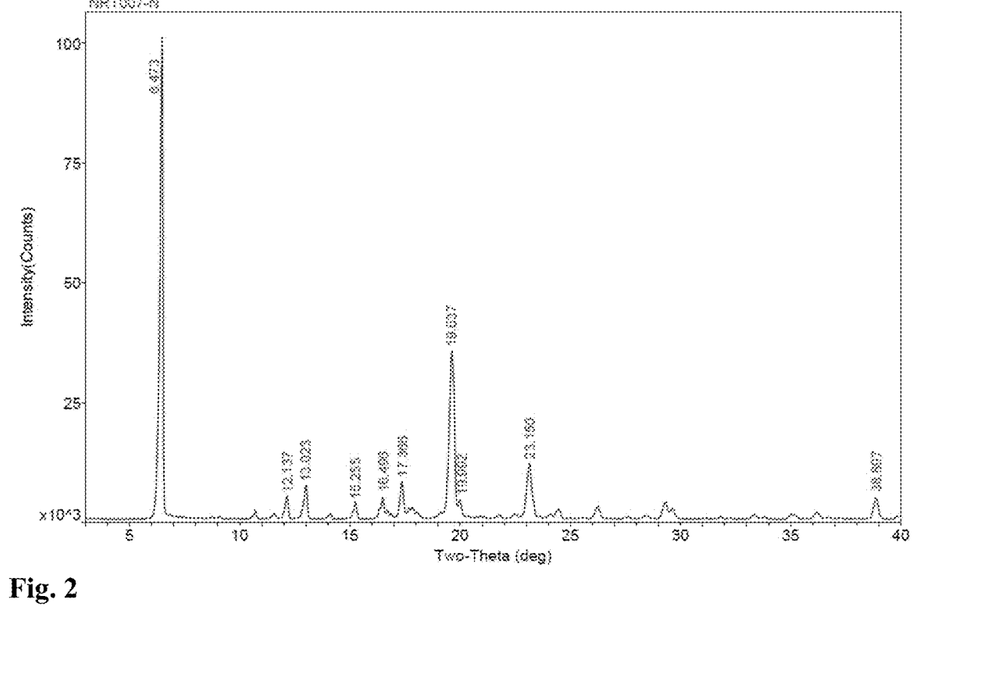
FIG. 2 is the XRPD spectrum of Crystalline Form A of Nintedanib that is commercially available.
Figure 3:
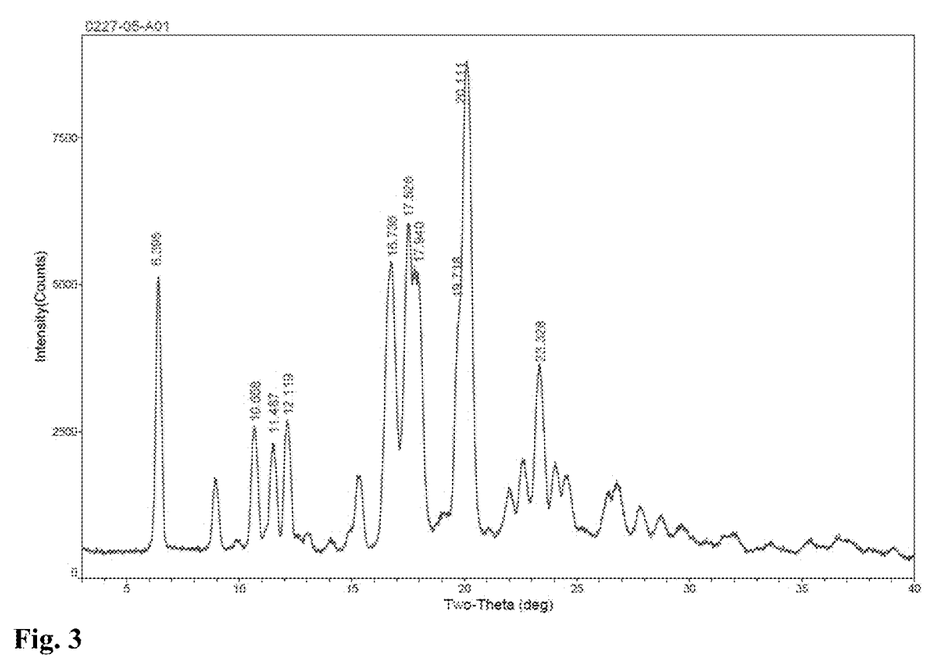
FIGS. 3 to 10 are the XRPD spectra of Crystalline Form C of Nintedanib generated in accordance with experiment numbers 0227-05-A01 to 0227-05-A08, respectively.
Figure 4:
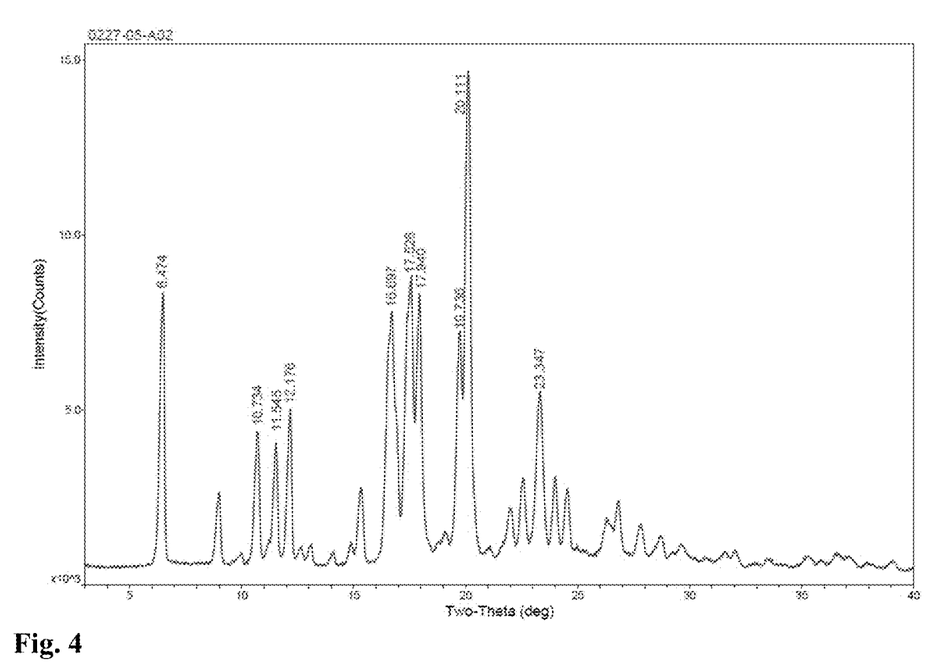
Figure 5:
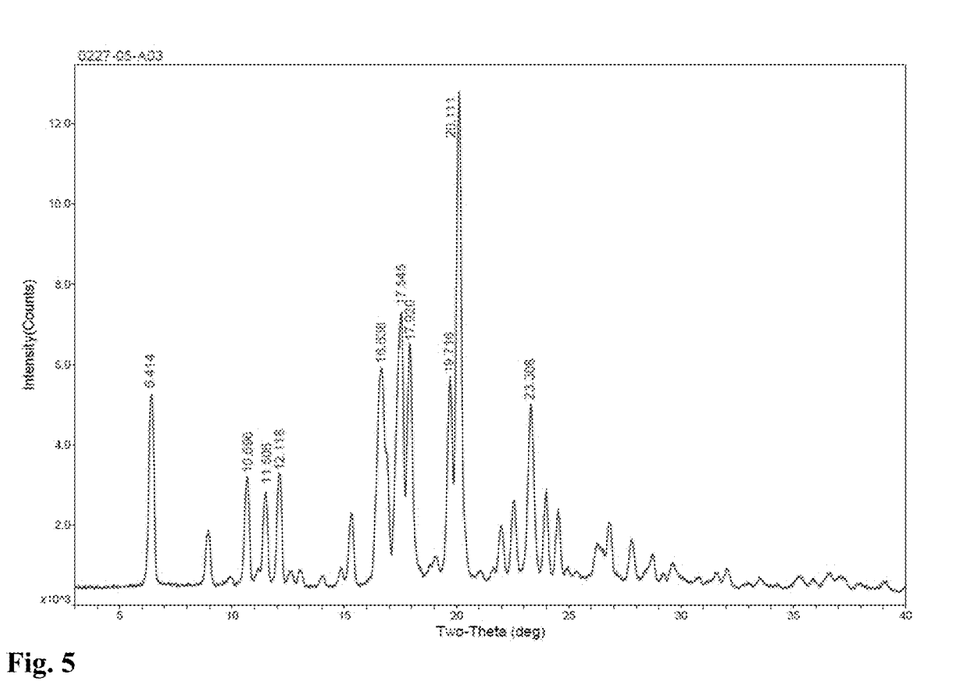
Figure 6:
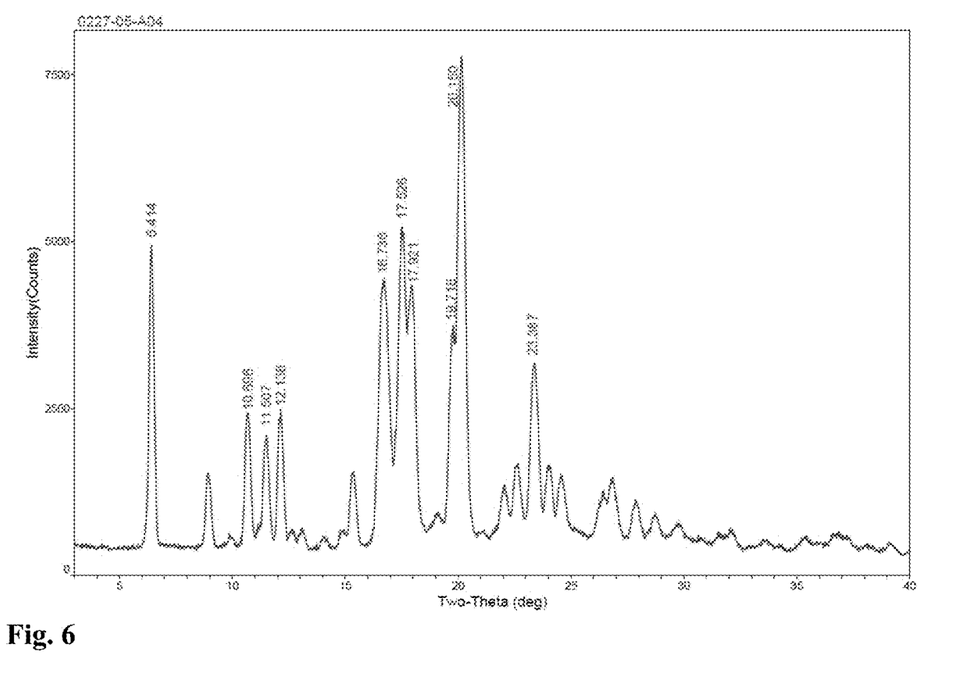
Figure 7:
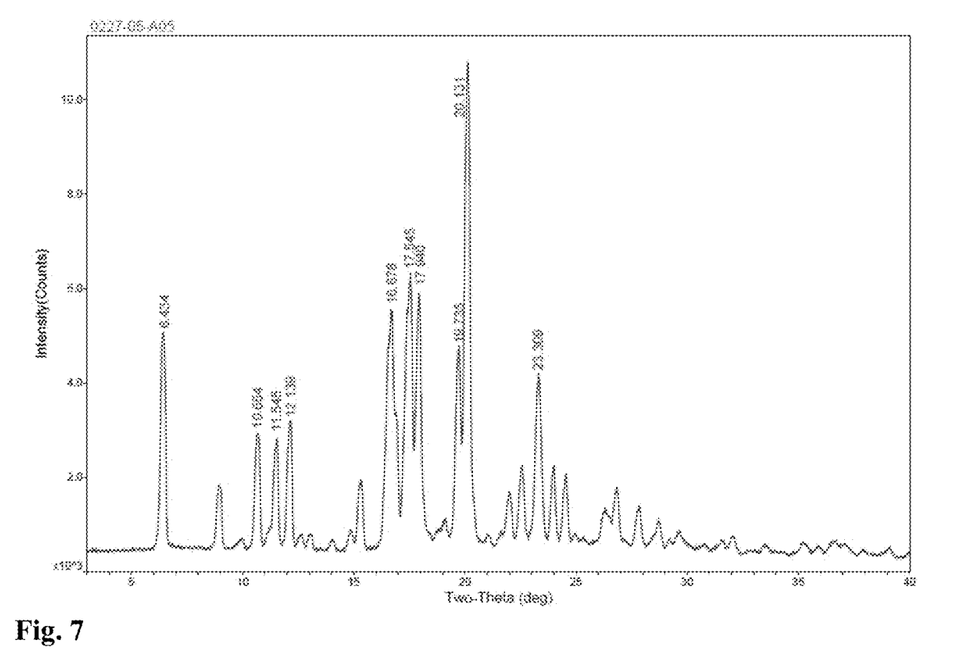
Figure 8:
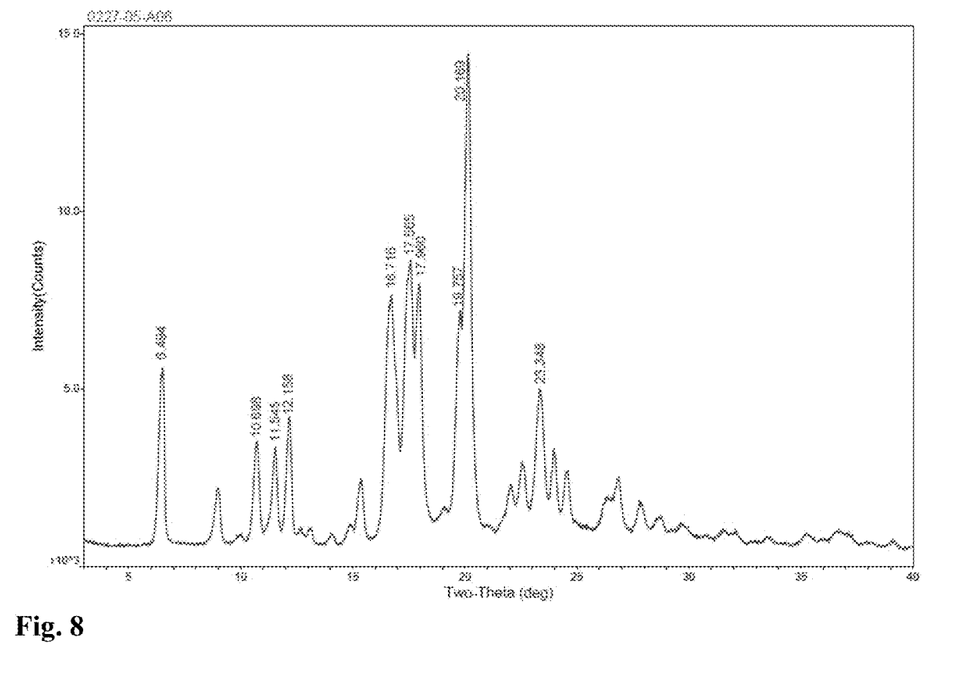
Figure 9:
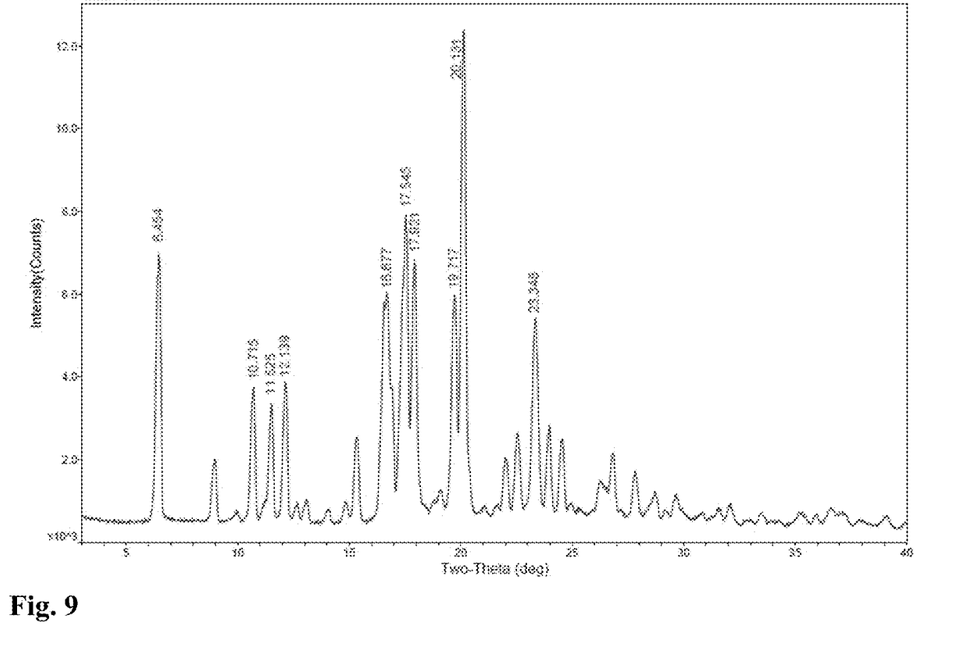
Figure 10:
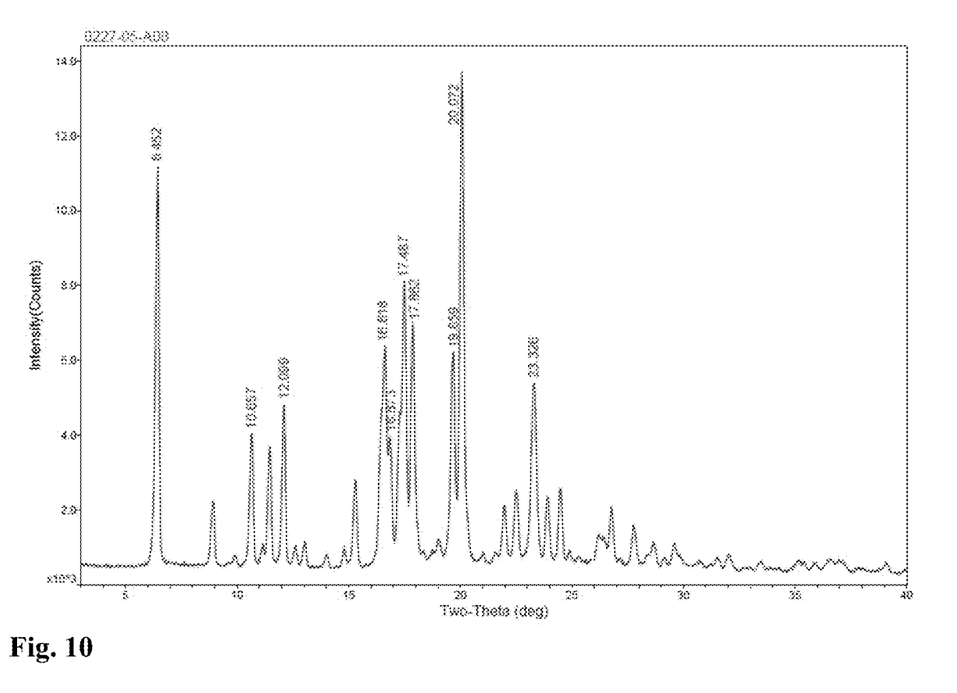

The crystalline form of a commercially available Nintedanib (Shanghai Baiteyin Pharmaceutical Technology Co., Ltd.) was determined and designated as Form A (its XRPD spectrum is shown in FIG. 2).

Eight samples of the commercially available Nintedanib (Shanghai Baiteyin Pharmaceutical Technology Co., Ltd.), about 30 g each, were weighed and placed in 8 vials for high performance liquid chromatography (HPLC) to which 1 mL solvent, as shown in the table below, were added respectively; the samples were suspended with magnetic stirring for 72 hours. After 72 hours, the supernatant was removed by centrifugation, and the solid was placed in a hood and dried at room temperature to obtain a solid of Crystalline Form C of Nintedanib. The experimental data and test results are shown in the table below. The XRPD spectra with respective experimental numbers are shown in FIGS. 3 to 10.

| Experimental No. | Solvent (v/v) | Target weight (mg) | Actual weight (mg) | Volume (mL) | Crystalline Form |
|---|---|---|---|---|---|
| 0227-05-A01 | acetonitrile | 30 | 29.3 | 1 | Crystalline Form C |
| 0227-05-A02 | isopropanol | 30 | 29.4 | 1 | Crystalline Form C |
| 0227-05-A03 | n-propyl alcohol | 30 | 30.3 | 1 | Crystalline Form C |
| 0227-05-A04 | 2-butanone | 30 | 29.3 | 1 | Crystalline Form C |
| 0227-05-A05 | 1,4-dioxane/water (9/1) | 30 | 29.7 | 1 | Crystalline Form C |

-continued

| Experimental No. | Solvent (v/v) | Target weight (mg) | Actual weight (mg) | Volume (mL) | Crystalline Form |
|---|---|---|---|---|---|
| 0227-05-A06 | heptane | 30 | 33 | 1 | Crystalline Form C |
| 0227-05-A07 | methanol water (9/1) | 30 | 29.8 | 1 | Crystalline Form C |
| 0227-05-A08 | acetone/water (9/1) | 30 | 28.9 | 1 | Crystalline Form C |

Example 3: Crystalline Form D of Nintedanib and its Preparation Method

About 20 g of the commercially available Nintedanib (Shanghai Baiteyin Pharmaceutical Technology Co., Ltd.) was weighed and added to a 10 mL-vial. 3 mL dichloromethane was added thereto, followed by vortexing for a few minutes and then filtering through a 0.22 μm organic filter membrane to obtain a filtrate in a 10 mL-vial. The vial containing the filtrate was sealed with parafilm through which 5-6 small holes were punched, and put in a hood for slow volatilization. The dried solid was Crystalline Form D of Nintedanib. The experimental data and test results are shown in the table below.

| Experimental No. | Solvent | Target weight (mg) | Actual weight (mg) | Volume (mL) | Crystalline Form |
|---|---|---|---|---|---|
| 0227-04-A07 | dichloromethane | 20 | 19 | 3 | Crystalline Form D |

The XRPD spectrum of Crystalline Form D of Nintedanib is shown in FIG. 11.

Example 4: Crystalline Form E of Nintedanib and its Preparation Method

Crystalline Form A of Nintedanib in the following experiment was purchased from Shanghai Baiteyin Pharmaceutical Technology Co., Ltd.; Crystalline Form B of Nintedanib was obtained with the preparation method in Example 1; Crystalline Form C of Nintedanib was obtained with the preparation method in Example 2.

2-3 mg of Crystalline Form A of Nintedanib was weighed, 1 mL water was added thereto, followed by vortexing for a few minutes and filtering through a 0.22 μm organic filter membrane, and the filtrate was added to a 1.8 mL HPLC vial containing 2-3 mg of Crystalline Form C of Nintedanib; the resultant was vortexed for a few minutes and filtered through a 0.22 μm organic filter membrane, and the filtrate was added to a 1.8 mL HPLC vial containing 10 mg of each of Crystalline Forms A, B, and C of Nintedanib; after magnetic stirring for 72 hours, the supernatant was removed by centrifugation, and the resultant solid was placed in a hood and dried at room temperature to obtain a solid as Crystalline Form E of Nintedanib. The experimental data and test results were shown in the table below.

3-5 mg of Crystalline Form A of Nintedanib was weighed, 1 mL acetone/water (9/1, v/v) was added thereto, followed by vortexing for a few minutes and filtering through a 0.22 μm organic filter membrane, and the filtrate was added to a 1.8 mL HPLC vial containing 3-5 mg of Crystalline Form B of Nintedanib; the resultant was vortexed for a few minutes and filtered through a 0.22 μm organic filter membrane, and the filtrate was added to a 1.8 mL HPLC vial containing 10 mg of each of Crystalline Forms A, B, and C of Nintedanib; after magnetic stirring for 72 hours, the supernatant was removed by centrifugation, and the resultant solid was placed in a hood and dried at room temperature to obtain a solid of Crystalline Form E of Nintedanib. The experimental data and test results are shown in the table below.

| Experimental No. | solvent | Target weight (mg) | Actual weight (mg) | Crystalline Form |
|---|---|---|---|---|
| 0227-11-A04 | water | 10 + 10 + 10 | 10.0 + 9.2 + 10.1 | Crystalline Form E |
| 0227-11-A05 | acetone/water (9/1) | 10 + 10 + 10 | 12.1 + 10.5 + 15.2 | Crystalline Form E |

Figure 12:
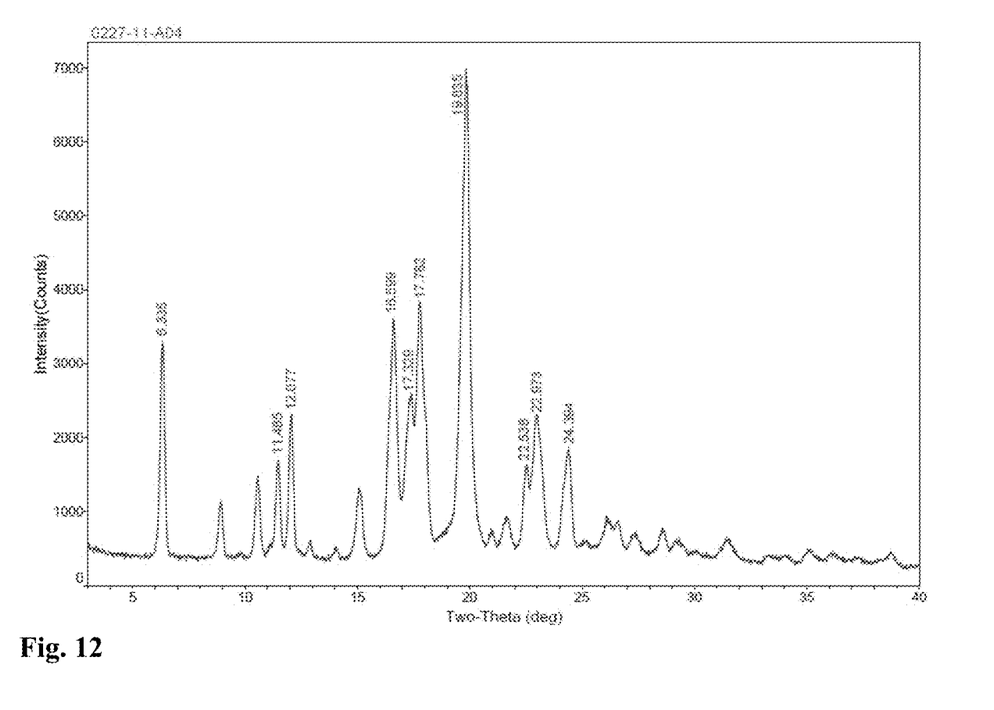
FIG. 12 is the XRPD spectrum of Crystalline Form E of Nintedanib according to the invention (experimental No. 0227-11-A04).

The XRPD spectrum of Crystalline Form E of Nintedanib (0227-11-A04) is shown in FIG. 12; the DSC profile (0227-11-A04) is shown in FIG. 13.

Figure 14:
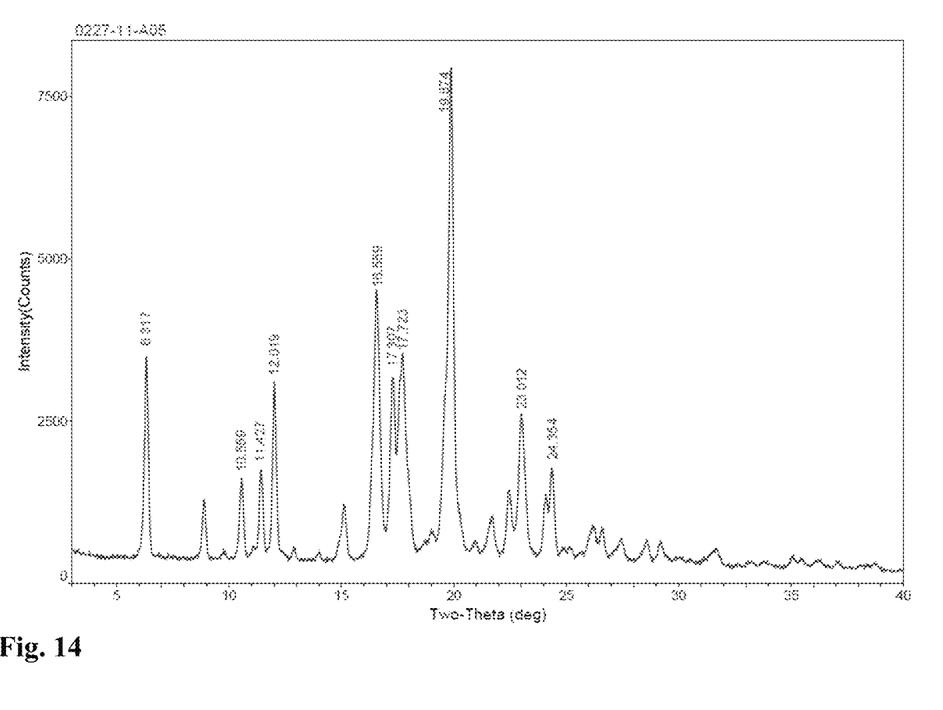
FIG. 14 is the XRPD spectrum of Crystalline Form E of Nintedanib according to the invention (with experimental No. 0227-11-A05).

The XRPD spectrum of Crystalline Form E of Nintedanib (0227-11-A05) is shown in FIG. 14.

Example 5: Crystalline Form F of Nintedanib and its Preparation Method 30 g of Nintedanib ethanesulfonate was added to 300 mL water, and pH of the solution was adjusted to about 10 with a saturated sodium carbonate solution under stirring at room temperature; 200 mL dichloromethane was added to the suspended solution, stirred for 15 minutes, allowed to stand for liquid separation, and the water layer was further extracted once with dichloromethane; the organic phase was combined, and the organic phase was washed twice with 100 mL water; after liquid separation and drying with anhydrous sodium sulfate, the solvent was removed by distilling under reduced pressure, and the resultant was dried by air blowing at 45° C. for 8 hours to obtain 27 g of a Nintedanib free base. 27 g of this sample was added to 140 mL ethanol, suspended under stirring for 3 days, filtered, and then dried by air blowing at 45° C. for 15-16 hours to obtain Crystalline Form F.

The XRPD spectrum of Crystalline Form F is shown in FIG. 15; its DSC profile is shown in FIG. 16.

Examples of Scaled-Up Preparation of Crystalline Forms of Nintedanib

Example 6: Scaled-Up Preparation of Crystalline Form C of Nintedanib 500 mg of commercially available Nintedanib (Shanghai Baiteyin Pharmaceutical Technology Co., Ltd.) was weighed, to which 15 mL acetone/water (9/1, v/v) was added, and suspended under stirring at room temperature for 72 hours; the supernatant was removed by centrifugation, and the solid obtained was placed in a hood and dried at room temperature to obtain a solid as Crystalline Form C of Nintedanib. The experimental data and test results are shown in the table below.

Crystalline Form B of Nintedanib was obtained with the preparation method in Example 1. 500 mg of Crystalline Form B of Nintedanib was weighed, to which 15 mL acetone/water (9/1, v/v) was added, and suspended under stirring at room temperature for 72 hours; the supernatant was removed by centrifugation, and the solid obtained was placed in a hood and dried at room temperature to obtain a solid as Crystalline Form C of Nintedanib. The experimental data and test results are shown in the table below.

| Experimental No. | Solvent (v/v) | Target weight (mg) | Actual weight (mg) | Volume (mL) | Crystalline Form |
|---|---|---|---|---|---|
| 0227-06-A01 | acetone/water (9/1) | 500 | 489.9 | 15 | Crystalline Form C |
| 0227-06-A02 | acetone/water (9/1) | 500 | 478.4 | 15 | Crystalline Form C |

Figure 17:
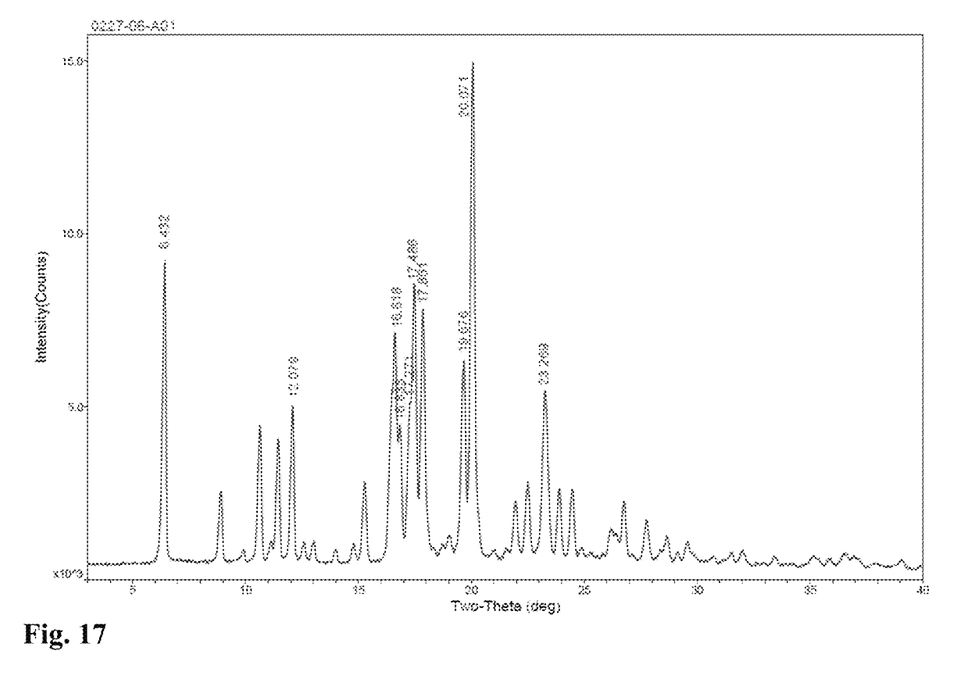
FIG. 17 is the XRPD spectrum of Crystalline Form C of Nintedanib according to the invention (with experimental No. 0227-06-A01).
Figure 18:
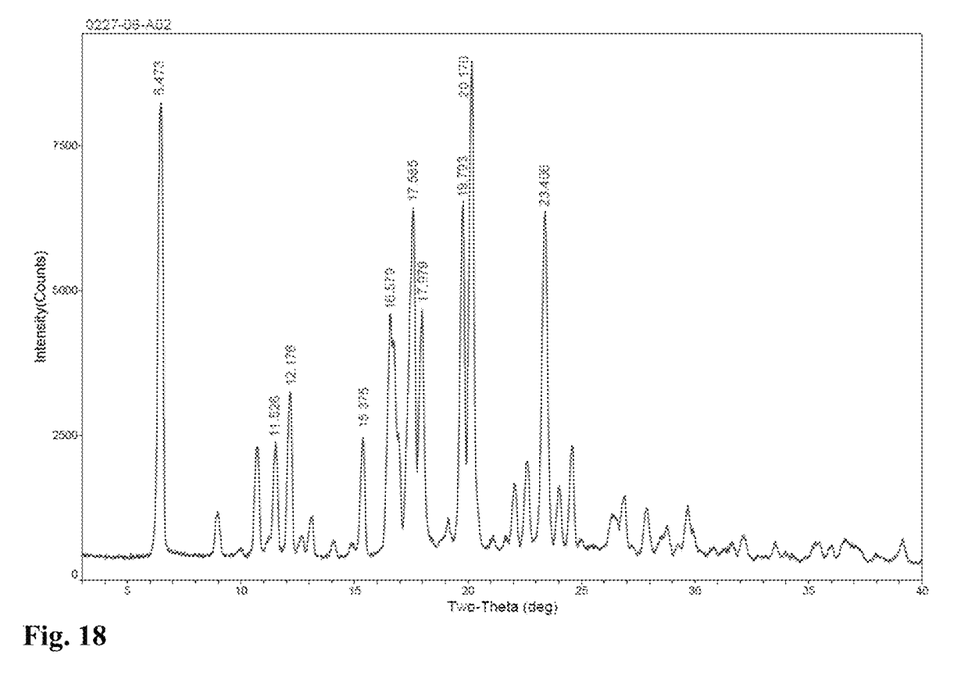
FIG. 18 is the XRPD spectrum of Crystalline Form C of Nintedanib according to the invention (with experimental No. 0227-06-A02).

The XRPD spectrum of Crystalline Form C of Nintedanib (0227-06-A01) is shown in FIG. 17. The XRPD spectrum of Crystalline Form C of Nintedanib (0227-06-A02) is shown in FIG. 18.

Example 7: Scaled-Up Preparation of Crystalline Form E of Nintedanib

Crystalline Form F of Nintedanib in the following experiment was obtained with the preparation method in Example 5.

Figure 19:
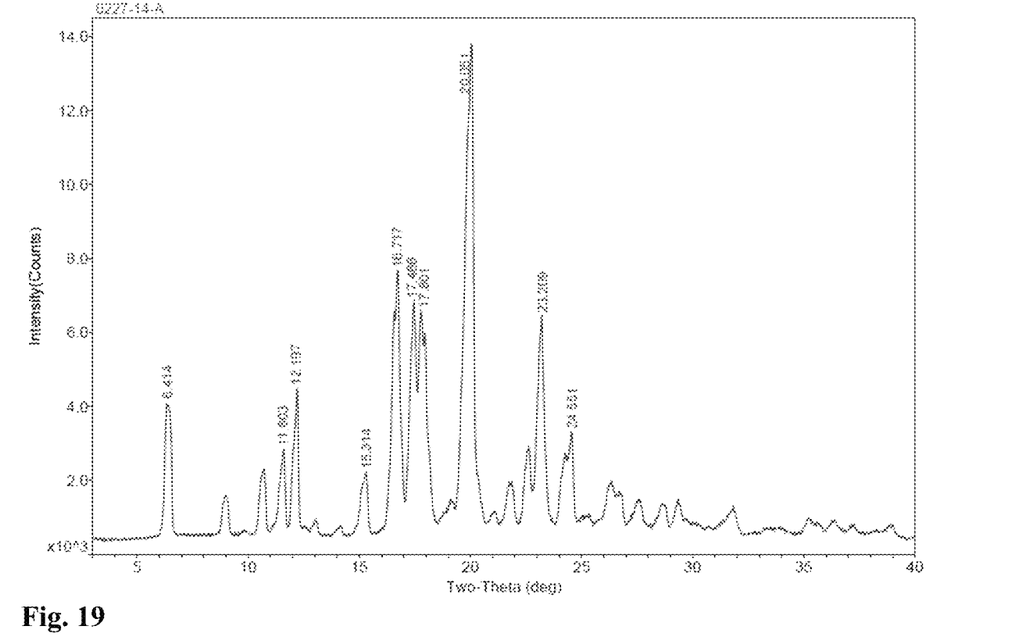
FIG. 19 is the XRPD spectrum of Crystalline Form E of Nintedanib in Example 7 according to the invention.

About 500 mg of Crystalline Form F of Nintedanib was weighed and added to a 30 mL vial, 15 mL water was added thereto, stirred homogenously with magnetic stirring before a small amount of Crystalline Form E was added thereto as seed crystal; after magnetic stirring under room temperature for 72 hours, a solid was obtained by centrifugation and dried at 40° C. for 2 days, thereby obtaining a solid as Crystalline Form E of Nintedanib (its XRPD spectrum is shown in FIG. 19).

Stability Test of Crystalline Forms of Nintedanib

Example 8: Stability Test of Nintedanib Nanosuspension

Figure 20:
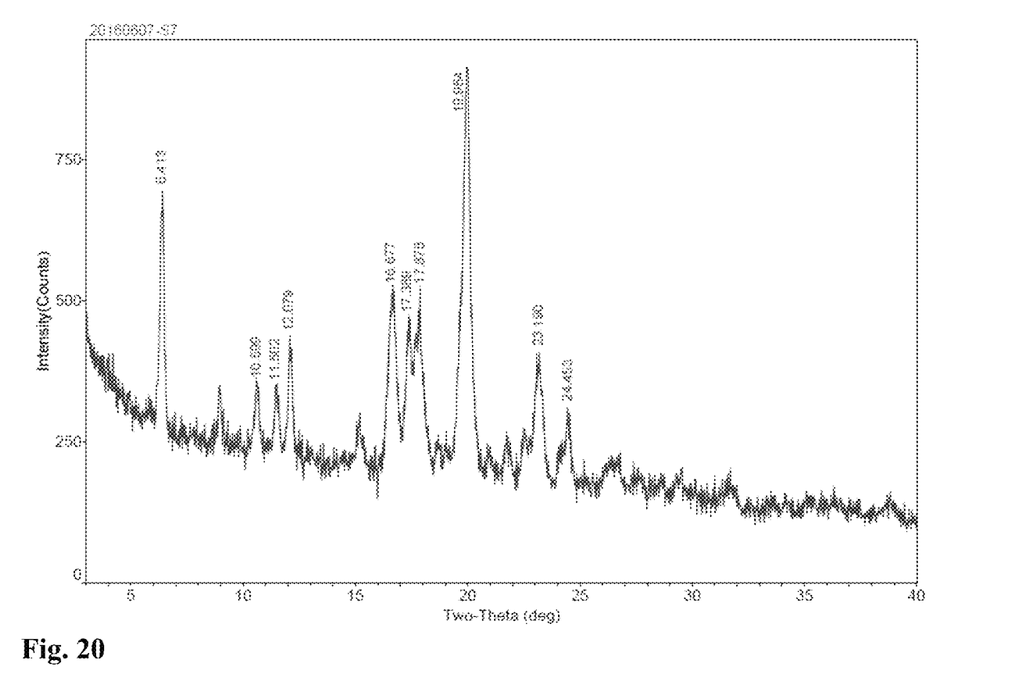
FIG. 20 is the XRPD spectrum of Crystalline Form E of Nintedanib in Example 8 according to the invention.

About 4.0 g of Crystalline Form F of Nintedanib obtained with the preparation method in Example 5 was weighed and dispersed and mixed in 200 mL of a 0.2% tyloxapol solution under stirring at room temperature. Next, the mixture of Nintedanib and tyloxapol were ground together with 200 micron zirconia grinding beads in a 160 mL NETZSCH® MINICER chamber. Particular characteristics of the formulated composition, e.g., particle size distribution, were varied by adjusting the grinding speed and duration. An exemplary speed and duration used were 3000 rpm for 20 minutes. After grinding, the particle size distribution of the Nintedanib particles was evaluated. After centrifugation and drying, the solid obtained was identified as Crystalline Form E of Nintedanib by XRPD (the XRPD spectrum is shown in FIG. 20).

The particle size and composition of an exemplary Nintedanib nanosuspension produced by the above ball milling process are shown in the table below.

| Components | Value w/v (%) |
|---|---|
| Nintedanib | 1 |
| Tyloxapol | 0.1 |
| Disodium ethylenediamine tetra-acetate | 0.01 |
| Sodium chloride | 0.75 |
| Ammonium benzyl dimethyl chloride | 0.005 |
| Suspending agent | 0.5 |
| Potassium phosphate buffer (10 mM) | 0.136 |
| Grinding speed and duration | 3000 rpm, 20 mins |
| D10/50/90 (micron) | 0.251/0.386/0.619 |

Figure 21:
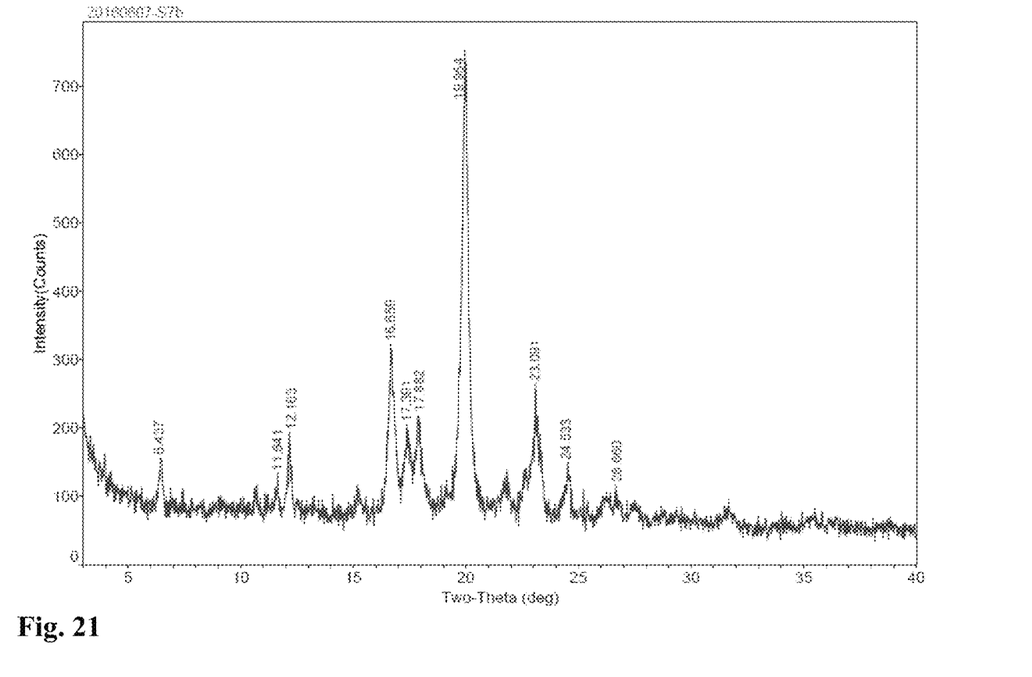
FIG. 21 is the XRPD spectrum of Crystalline Form E of Nintedanib after being kept in an incubator at 60° C. for 28 days in accordance with Example 8 of the present invention.
Figure 22:
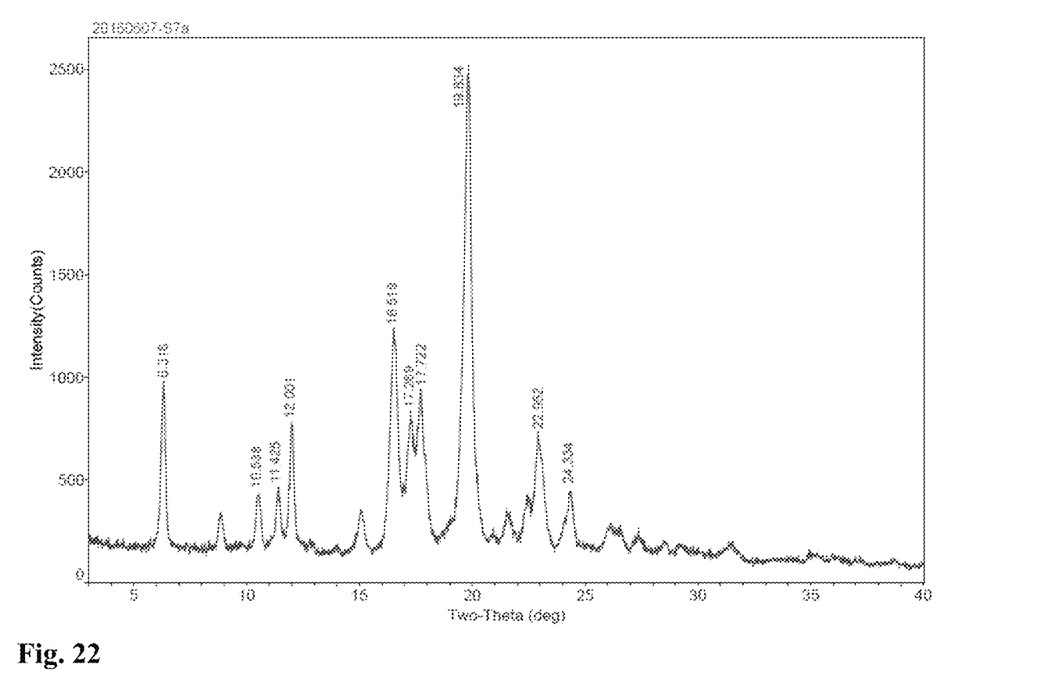
FIG. 22 is the XRPD spectrum of Crystalline Form E of Nintedanib after being kept in an incubator at 4° C. for 28 days in accordance with Example 8 of the present invention.

A stability test was carried on the Nintedanib nanosuspension produced by the above ball milling process. The Nintedanib nanosuspension samples were placed in incubators respectively at 60° C. and 4° C. for 28 days; afterwards, they were taken and centrifuged, and washed with water to remove residual excipient solution; the solid obtained was dried by air blowing at 30° C. for 1-2 days, and then taken out when there was no obvious residual moisture on the surface of the sample for XRPD measurement. The results suggested that the stability of the above nanosuspension was maintained under different storage environments, and its crystalline form remained as Crystalline Form E. The measurement result of the XRPD spectrum of the samples after being placed in an incubator at 60° C. for 28 days is shown in FIG. 21. The measurement result of the XRPD spectrum of the samples after being placed in an incubator at 4° C. for 28 days is shown in FIG. 22.

Example 9: Stability Test of Crystalline Form F of Nintedanib

Crystalline Form F of Nintedanib obtained with the preparation method in Example 5 was placed in a polyethylene plastic bag, the plastic bag was then placed in a desiccator with no humidity control at room temperature for three months (from April 12 to July 12). The XRPD spectra on April 12 and July 12 were determined respectively (See FIG. 15 for the XRPD spectrum of the sample before the placement and FIG. 23 for the XRPD spectrum of the sample three months after the placement), all the measurements showed a result of Crystalline Form F.

The invention claimed is:

1. A crystalline form of free base 3-Z-[1-(4-(N-((4-methyl-piperazin-1-yl)-methylcarbonyl)-N-methyl-amino)-phenylamino)-1-phenyl-methylene]-6-methoxycarbonyl-2-indolinone, characterized by having an X-ray powder diffraction (XRPD) pattern with a peak at 2θ value of 6.4±0.2, and at least one peak at 2θ value selected from 16.6±0.2, 17.4±0.2, 17.8±0.2, and 19.9±0.2.

2. The crystalline form according to claim 1, wherein the crystalline form is characterized by an XRPD pattern with peaks at 2θ values of 6.4±0.2, 16.6±0.2, 17.4±0.2, 17.8±0.2, and 19.9±0.2.

3. The crystalline form according to claim 1, wherein the crystalline form is characterized by an XRPD pattern with peaks at 2θ values of 6.4±0.2, 12.0±0.2, 16.6±0.2, 17.4±0.2, 17.8±0.2, and 19.9±0.2.

4. The crystalline form according to claim 3, wherein the crystalline form has a melting temperature of 245° C.±5° C.

5. The crystalline form according to claim 3, wherein the crystalline form has a melting temperature of 255° C.±5° C.

6. The crystalline form according to claim 2, wherein the crystalline form is characterized by an XRPD pattern with peaks at 2θ values of 6.4±0.2, 16.6±0.2, 17.4±0.2, 17.8±0.2, 19.9±0.2, and 23.3±0.2.

7. The crystalline form according to claim 1, wherein the crystalline form is characterized by an XRPD pattern with peaks at 2θ values of 4.8±0.2, 5.6±0.2, 6.4±0.2, 17.4±0.2, and 19.9±0.2.

8. A crystalline form of free base 3-Z-[1-(4-(N-((4-methyl-piperazin-1-yl)-methylcarbonyl)-N-methyl-amino)-phenylamino)-1-phenyl-methylene]-6-methoxycarbonyl-2-indolinone, characterized by having an XRPD pattern with peaks at 2θ values of 11.2±0.2, 14.8±0.2, 16.4±0.2, 17.0±0.2, and 21.0±0.2.

9. The crystalline form according to claim 1, wherein crystalline form has an XRPD spectrum as shown in FIG. 12, FIG. 14, FIG. 19, FIG. 20, FIG. 21, or FIG. 22.

10. The crystalline form according to claim 9, wherein the crystalline form has a Differential Scanning calorimetry (DSC) profile as shown in FIG. 13.

11. The crystalline form according to claim 1, wherein the crystalline form has a Differential Scanning calorimetry (DSC) profile as shown in FIG. 13.

12. The crystalline form according to claim 1, wherein the crystalline form has an XRPD spectrum as shown in FIG. 15 or FIG. 23.

13. The crystalline form according to claim 12, wherein the crystalline form has a DSC profile as shown in FIG. 16.

14. The crystalline form according to claim 1, wherein the crystalline form has a DSC profile as shown in FIG. 16.

15. The crystalline form according to claim 1, wherein the crystalline form has an XRPD spectrum as shown in FIG. 3, FIG. 4, FIG. 5, FIG. 6, FIG. 7, FIG. 8, FIG. 9, FIG. 10, FIG. 17, or FIG. 18.

16. The crystalline form according to claim 1, wherein the crystalline form has an XRPD spectrum as shown in FIG. 11.

17. The crystalline form according to claim 8, wherein the crystalline form has an XRPD spectrum as shown in FIG. 1.

18. An ophthalmic formulation comprising the crystalline form according to claim 1 and at least one pharmaceutically acceptable carrier.

19. A method of treating an eye disease in an individual in need, comprising administering to the individual the ophthalmic formulation according to claim 18, wherein the eye disease is selected from: age-related macular degeneration (AMD), angiogenic eye disease, atrophic changes of retinal pigment epithelium (RPE), choroidal neovascularization (CNV), choroidal retinal vein occlusion, conjunctival degeneration (pinguecula) with slow proliferation, conjunctival papilloma, diabetic macular edema, diabetic retinopathy, hyperemia, hyperemia associated with pterygium, hyperthyroidism-induced hyperemia, hypertrophic changes of retinal pigment epithelium (RPE), immune or surgical-related dry eyes, intraretinal edema, macular edema, macular edema due to retinal vein occlusion, neovascular glaucoma (NVG), ocular cancer, pterygium conjunctivae, pterygium recurrence, Steven Johnson syndrome, stye, and subretinal edema.

20. The method according to claim 19, wherein the angiogenic eye disease is selected from corneal angiogenesis following keratitis, corneal transplantation or keratoplasty, and corneal angiogenesis due to hypoxia retinal detachment.

* * * * *